(12) United States Patent
Wurst et al.

(10) Patent No.: US 11,065,364 B2
(45) Date of Patent: Jul. 20, 2021

(54) COMBINATION WITH ALBUMIN, IN PARTICULAR FOR TREATING A CARTILAGE DEFECT

(71) Applicant: TETEC Tissue Engineering Technologies AG, Reutlingen (DE)

(72) Inventors: Helmut Wurst, Kusterdingen (DE); Nils Clausen, Tuebingen (DE); Nina Baldassi, Tuebingen (DE)

(73) Assignee: TETEC Tissue Engineering Technologies AG, Reutlingen (DE)

( * ) Notice: Subject to any disclaimer, the term of this patent is extended or adjusted under 35 U.S.C. 154(b) by 18 days.

(21) Appl. No.: 16/329,647

(22) PCT Filed: Aug. 28, 2017

(86) PCT No.: PCT/EP2017/071560
§ 371 (c)(1),
(2) Date: Feb. 28, 2019

(87) PCT Pub. No.: WO2018/041784
PCT Pub. Date: Mar. 8, 2018

(65) Prior Publication Data
US 2019/0192733 A1    Jun. 27, 2019

(30) Foreign Application Priority Data
Aug. 29, 2016  (DE) .................... 10 2016 216 182.2

(51) Int. Cl.
| | | |
|---|---|---|
| *A61L 27/22* | (2006.01) | |
| *A61L 27/38* | (2006.01) | |
| *A61L 27/52* | (2006.01) | |
| *A61K 35/32* | (2015.01) | |
| *A61K 35/30* | (2015.01) | |
| *C07K 14/76* | (2006.01) | |
| *A61K 35/39* | (2015.01) | |
| *A61K 35/37* | (2015.01) | |
| *A61K 35/28* | (2015.01) | |
| *A61K 38/38* | (2006.01) | |
| *A61K 31/715* | (2006.01) | |
| *A61L 27/20* | (2006.01) | |

(52) U.S. Cl.
CPC .......... *A61L 27/227* (2013.01); *A61K 31/715* (2013.01); *A61K 35/28* (2013.01); *A61K 35/30* (2013.01); *A61K 35/32* (2013.01); *A61K 35/37* (2013.01); *A61K 35/39* (2013.01); *A61K 38/38* (2013.01); *A61L 27/20* (2013.01); *A61L 27/38* (2013.01); *A61L 27/3826* (2013.01); *A61L 27/3834* (2013.01); *A61L 27/52* (2013.01); *C07K 14/76* (2013.01); *A61L 2400/06* (2013.01)

(58) Field of Classification Search
CPC ........ A61L 27/227; A61L 27/38; A61L 27/20; A61L 27/3826; A61L 27/3834; A61L 27/52; A61L 2400/06; A61K 35/39; A61K 35/32; A61K 35/30; A61K 31/714; A61K 38/38; A61P 19/00; A61P 19/02; C07K 14/76
See application file for complete search history.

(56) References Cited

U.S. PATENT DOCUMENTS

| | | |
|---|---|---|
| 2002/0076810 A1 | 6/2002 | Radice et al. |
| 2010/0322993 A1 | 12/2010 | Mollenhauer et al. |
| 2012/0258147 A1 | 10/2012 | Mollenhauer et al. |
| 2013/0052736 A1 | 2/2013 | Wurst et al. |

OTHER PUBLICATIONS

Gao et al, Thiolated Human Serum Albumin Cross-Linked Dextran Hydrogels as a Microscale Delivery System, Royal Society of Chemistry, Soft Matter, 10, 4869-4874. (Year: 2014).*
Gao et al, Thiolated Human Serum-Albumin Cross-Linked Dextran as a Macroscale Delivery System, Royal Society of Chemisrty, pp. 4869-4874. (Year: 2014).*
Zhang et al, Detailed Characterization of an Injectable Hyaluronic Acid—Polyaspartylhydrazide Hydrogel for Drug Delivery, Carbohydrates Polymers, 85: 217-225 (Year: 2011).*
Gao et al., "Thiolated human serum albumin cross-linked dextran hydrogels as macroscale delivery system." (2014) Soft Matter 10:4869-4874. DOI: 10.1039/c4sm00648h.
Zhang et al., "Detailed characterization of an injectable hyaluronic acid-polyaspartylhydrazide hydrogel for protein delivery." (2011) Carbohydrate Polymers 85:717-725.
English translation of International Search Report dated Mar. 14, 2019, of corresponding International Patent Application No. PCT/EP2017/071560.

* cited by examiner

*Primary Examiner* — Carlos A Azpuru
(74) *Attorney, Agent, or Firm* — Lewis Kohn & Walker LLP; David M. Kohn

(57) ABSTRACT

A combination comprising, spatially separate from one another, a first component and a second component, where the first component comprises crosslinkable albumin and the second component comprises a polymer, wherein non-terminal monomer units of the polymer comprise at least partially, more particularly only partially, an albumin-crosslinking group. Additionally disclosed is a reaction product obtainable by means of the combination, to a medical device, to a medicinal product for innovative therapies, to a kit, to a discharge apparatus, and to a functionalized hyaluronic acid.

16 Claims, No Drawings

COMBINATION WITH ALBUMIN, IN PARTICULAR FOR TREATING A CARTILAGE DEFECT

CROSS-REFERENCE TO RELATED APPLICATIONS

This application is a United States National Stage Application claiming the benefit of priority under 35 U.S.C. 371 from International Patent Application No. PCT/EP2017/071560 filed Aug. 28, 2017, which claims the benefit of priority from German Patent Application Serial No. 10 2016 216 182.2 filed Aug. 29, 2016, the entire contents of which are herein incorporated by reference.

BACKGROUND OF THE INVENTION

The present invention relates to a combination, to a reaction product, preferably in the form of a hydrogel, to a medical device, to a medicinal product for innovative therapies, to a kit, to a discharge apparatus, to a method for producing the combination, to a method for producing the reaction product, to the use of a polymer for crosslinking albumin, and to a hyaluronic acid functionalized by albumin-crosslinking groups.

Known from DE 10 2008 008 071 A1 is an injectable, biocompatible combination of crosslinkable serum albumin and also the crosslinker dithio-polyethylene glycol (dithio-PEG).

A fundamental drawback of dithio-PEG, however, is that it is complicated and expensive to produce. Another factor is that it is necessary to ensure that PEG is functionalized with thiol groups at both chain ends, since monofunctionalized PEG acts to inhibit the crosslinking of albumin.

This raises the cost and complexity associated with the production and, in particular, purification of the crosslinker. A further drawback is that dithio-PEG undergoes only slow breakdown in the body and must be excreted via the kidneys.

SUMMARY OF THE INVENTION

The present invention is therefore based on the problem of providing an alternative combination product which avoids shortcomings known from the prior art and in particular is both easier to produce and more biocompatible than conventional combination products.

A further problem forming a basis for the present invention is that of providing a functionalized hyaluronic acid which in particular may be a constituent of the combination product referred to in the previous paragraph.

These problems are solved by: A combination product comprising a first component and a second component, wherein the first component comprises crosslinkable albumin and the second component comprises a polymer, wherein non-terminal monomer units of the polymer comprise at least partially an albumin-crosslinking group and further wherein the first component and the second component are spatially separate; a medical device or a medicinal product for innovative therapies comprising a combination product comprising a first component and a second component, wherein the first component comprises crosslinkable albumin and the second component comprises a polymer, wherein non-terminal monomer units of the polymer comprise at least partially an albumin-crosslinking group and further wherein the first component and the second component are spatially separate; a kit or a discharge apparatus comprising a combination product comprising a first component and a second component, wherein the first component comprises crosslinkable albumin and the second component comprises a polymer, wherein non-terminal monomer units of the polymer comprise at least partially an albumin-crosslinking group and further wherein the first component and the second component are spatially separate; a use for a combination product comprising a first component and a second component, wherein the first component comprises crosslinkable albumin and the second component comprises a polymer, wherein non-terminal monomer units of the polymer comprise at least partially an albumin-crosslinking group and further wherein the first component and the second component are spatially separate; and a functionalized hyaluronic acid wherein every third to thousandth, more particularly ever tenth to five-hundredth, preferably every twentieth to hundredth non-terminal monomer unit of the hyaluronic acid comprises an albumin-crosslinking group. Preferred embodiments are defined in the dependent claims. The wording of all the claims is hereby made part of the present description by express reference. Additional aspects of the invention are disclosed in the description.

DETAILED DESCRIPTION OF THE INVENTION

According to a first aspect, the invention relates to a combination which comprises, spatially separate from one another, a first component and a second component.

The first component comprises crosslinkable albumin.

The second component comprises a polymer, where non-terminal monomer units of the polymer comprise at least partially, more particularly only partially, an albumin-crosslinking group.

The combination may be referred to in the context of the present invention also as a combination product.

The inventors have recognized that through functionalization of non-terminal monomer units ("internal functionalization) with albumin-crosslinking groups it is possible to produce a polymeric crosslinker for albumin where the loading of the crosslinker with the albumin-crosslinking groups can be controlled more effectively than in the case, for example, of the dithio-PEG known from the prior art. Since in general there are a multiplicity of non-terminal monomer units available for functionalization, there is no longer any risk of the formation of monofunctionalized polymers, with possible inhibitory effect on the crosslinking of albumin.

Moreover, production of the polymeric crosslinker is simplified, since there is no need for strict functionalization of all terminal monomer units, as in the case of the dithio-PEG known from the prior art. This leads to reduced production times and costs.

The combination is suitable in particular for the treatment, preferably reconstruction, of a cartilage defect, more particularly of an articular cartilage defect or intervertebral disc defect.

The expression "crosslinkable albumin" is intended in the sense of the present invention to refer to an albumin which by virtue of its chemical nature, more particularly on the basis of functionalization and/or derivatization, can be crosslinked by means of a crosslinker, more particularly by means of the polymer provided in accordance with the invention. The crosslinking may be based in particular on hydrogen bonds, ionic bonds and/or covalent bonds between the albumin and the crosslinker, more particularly the polymer provided in accordance with the invention. The crosslinking of the albumin is preferably based on the formation of covalent bonds between the albumin and the crosslinker, more particularly the polymer provided in accordance with the invention.

The expression "non-terminal monomer units" is intended in the sense of the present invention to refer to monomer units which are located between terminal monomer units of the polymer.

The expression "albumin-crosslinking group" or "albumin-crosslinking groups" is intended in the sense of the present invention to refer to a group or groups which brings or bring about crosslinking of albumin through reaction with functional groups of the albumin, preferably with formation of covalent bonds or linkages.

The expression "functionalized" or "functionalize" is intended in the sense of the present invention to refer to any—completed—process by which the polymer or albumin is endowed with a function which it normally does not possess, by means, for example, of the addition of groups onto the polymer or albumin, respectively.

In one preferred embodiment the non-terminal monomer units are constituents of a backbone or a main chain of the polymer.

In another embodiment the non-terminal monomer units are part of a side chain of the polymer.

In a further embodiment, moreover, terminal monomer units of the polymer comprise an albumin-crosslinking group. In this case the albumin-crosslinking groups of the terminal monomer units may be the same albumin-crosslinking groups as for the non-terminal monomer units. Furthermore, all the terminal monomer units of the polymer or only some of them may comprise an albumin-crosslinking group.

In another embodiment terminal monomer units of the polymer are free from an albumin-crosslinking group.

In another embodiment less than 20%, more particularly less than 10%, preferably less than 5% of the non-terminal monomer units comprise an albumin-crosslinking group.

Preferably on average, i.e. per polymer molecule, more than two or three, more particularly more than four, five, six, seven or eight, non-terminal monomer units comprise an albumin-crosslinking group.

In another embodiment every third monomer unit to thousandth monomer unit, more particularly every tenth monomer unit to five-hundredth monomer unit, preferably every twentieth monomer unit to hundredth monomer unit, comprises an albumin-crosslinking group. The monomer units mentioned in this paragraph are preferably non-terminal monomer units of the polymer.

In another embodiment the polymer has a degree of substitution of 33 to 0.1, more particularly 10 to 0.2, preferably 5 to 1 thiol groups per 100 monomer units, for example per 100 glucuronic acid units, anhydroglucose units or non-saccharidic monomer units. In other words, 33 to 0.1, more particularly 10 to 0.2, preferably 5 to 1, per 100 monomer units, for example per 100 glucuronic acid units, anhydroglucose units or non-saccharidic monomer units, of functional groups originally present, for example OH groups (hydroxy groups), may have been replaced by thiol groups (SH groups) or substituents carrying thiol groups.

In another embodiment the polymer is a linear, i.e. unbranched, polymer.

In an alternative embodiment the polymer is a branched or multi-armed, more particularly three- or four-armed, polymer.

In another embodiment the polymer is a hydrophilic polymer. For suitable hydrophilic polymers, reference may be made to the observations below.

In one useful embodiment the polymer is a biocompatible polymer, i.e. a polymer which is unobjectionable from a medical standpoint.

In another embodiment the polymer has an average molecular weight of 3 kDa to 10 000 kDa, more particularly 5 kDa to 1000 kDa, preferably 10 kDa to 100 kDa.

According to one particularly preferred embodiment, the polymer is a polymer functionalized by the albumin-crosslinking groups.

The polymer is preferably a polymer which is selected from the group consisting of polysaccharide functionalized by albumin-crosslinking groups, muco-polysaccharide functionalized by albumin-crosslinking groups, protein functionalized by albumin-crosslinking groups, synthetic polymer functionalized by albumin-crosslinking groups, and combinations of at least two of the stated functionalized polymers.

With further preference the polymer is selected from the group consisting of hyaluronic acid functionalized by albumin-crosslinking groups, carboxymethylcellulose functionalized by albumin-crosslinking groups, dextran functionalized by albumin-crosslinking groups, polyvinyl alcohol functionalized by albumin-crosslinking groups, polyvinylpyrrolidone functionalized by albumin-crosslinking groups, and combinations of at least two of the stated functionalized polymers.

The polymers mentioned in the preceding paragraphs have the advantage in particular that they are notable for greater biological compatibility by comparison with dithio-PEG, and at least in part for more rapid in vivo degradation or in vivo absorption.

In another embodiment the combination, more particularly the second component, is free from polyethylene glycol (PEG) and/or free from a functionalized polyethylene glycol, such as, for example, dithio-polyethylene glycol (dithio-PEG).

According to one particularly preferred embodiment, the polymer is a hyaluronic acid functionalized by albumin-crosslinking groups. The use of hyaluronic acid as a scaffold for the polymer has the advantage that it is a substance of particular body affinity.

Preferably every third repeating disaccharide unit to thousandth repeating disaccharide unit, more particularly every tenth repeating disaccharide unit to five-hundredth repeating disaccharide unit, preferably every twentieth repeating disaccharide unit to hundredth repeating disaccharide unit, of the functionalized hyaluronic acid is functionalized by an albumin-crosslinking group.

With particular preference glucuronic acid units of the hyaluronic acid and/or of the disaccharide units are functionalized by an albumin-crosslinking group.

In another embodiment the albumin-crosslinking or albumin-reactive groups are each linked via a linker unit covalently to the carboxy carbon atom of the glucuronic acid units.

The linker unit preferably possesses the formula I below

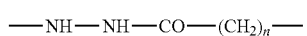
(formula I)

where n is an integer from 1 to 12, more particularly 2 to 4, preferably 2.

Alternatively, the linker unit preferably possesses the formula II below

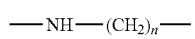  (formula II)

where n is an integer from 1 to 12, more particularly 2 to 4, preferably 2.

In one preferred embodiment the albumin-crosslinking group and/or the albumin-crosslinking groups is/are a nucleophilic group and/or nucleophilic groups, more particularly Michael donor group and/or Michael donor groups, preferably thiol group and/or thiol groups (SH group and/or SH groups) and/or thiolate group and/or thiolate groups ($S^-$ group and/or $S^-$ groups). The albumin-crosslinking group and/or the albumin-crosslinking groups is/are preferably a thiol group and/or thiol groups.

In one particularly preferred embodiment the polymer is a hyaluronic acid functionalized by thiol groups and/or thiolate groups, i.e. thiol- and/or thiolate-functionalized hyaluronic acid. With more particular preference the polymer is a hyaluronic acid functionalized by thiol groups.

In another embodiment the polymer comprises a fraction of 5 wt % to 3000 wt %, more particularly 10 wt % to 1000 wt %, preferably 50 wt % to 200 wt %, based on the dry weight, of the first component, more particularly of the crosslinkable albumin and of an unfunctionalized hyaluronic acid optionally present therein.

In another embodiment the second component further comprises salts, more particularly a buffer such as dihydrogenphosphate-hydrogenphosphate buffer and/or carbonic acid-hydrogencarbonate buffer.

In another embodiment the second component is in the form of an aqueous liquid, particularly in the form of an aqueous suspension or aqueous solution, preferably in the form of an aqueous solution.

The crosslinkable albumin in another embodiment is crosslinkable serum albumin, i.e. a crosslinkable albumin obtained from blood serum.

Alternatively, the crosslinkable albumin may be a synthetic albumin, i.e. an albumin produced in a chemical laboratory or comparable facility, or a recombinantly produced albumin.

Moreover, the albumin may be human or xenogenic, more particularly porcine, bovine or equine, in origin.

In accordance with the invention it is preferred, however, if the crosslinkable albumin is an albumin of human origin.

In another embodiment the crosslinkable albumin is a functionalized albumin, more particularly an albumin functionalized by electrophilic groups, more particularly Michael acceptor groups, preferably thiol-reactive groups. The expression "thiol-reactive groups" is intended in the sense of the present invention to refer to functional groups which are capable of reacting with thiol groups, preferably with formation of covalent bonds or linkages.

The groups mentioned in the preceding paragraph are preferably selected from the group consisting of maleimide groups, vinyl sulfone groups, acrylate groups, alkyl halide groups, azirine groups, pyridyl groups, thionitrobenzoic acid groups, arylating groups, and combinations of at least two of the stated functional groups.

Expressed alternatively, the albumin is preferably functionalized by groups which are selected from the group consisting of maleimide groups, vinyl sulfone groups, acrylate groups, alkyl halide groups, azirine groups, pyridyl groups, thionitrobenzoic acid groups, arylating groups, and combinations of at least two of the stated functional groups.

According to one particularly preferred embodiment, the crosslinkable albumin is an albumin functionalized by maleimide groups, i.e. maleimide-functionalized albumin, preferably a serum albumin functionalized by maleimide groups, i.e. maleimide-functionalized serum albumin.

In another embodiment the combination is a biocompatible, more particularly medically active, preferably therapeutically active combination.

The combination, more particularly the first component and/or the second component, preferably the first component, in another embodiment further comprises cells, more particularly mammalian cells, preferably selected from the group consisting of musculoskeletal cells, metabolism-regulating glandular cells, islet cells, melatonin-producing cells, progenitor cells, stem cells, more particularly mesenchymal stem cells, and combinations of at least two of the stated types of cell.

The musculoskeletal cells are preferably stem cells, chondrocytes, osteocytes, fibrochondrocytes, or a combination of at least two of the stated types of cell.

The autologous cells are preferably autologous chondrocytes, autologous intervertebral disc chondrocytes, autologous stem cells, autologous mesenchymal stem cells, or a combination of at least two of the stated types of cell.

In another embodiment the combination, more particularly the first component and/or the second component, preferably the first component, comprises at least one active ingredient, more particularly active pharmaceutical or biological ingredient.

The active ingredient is preferably selected from the group consisting of antibiotic, anti-inflammatory, metabolic hormone, chondroprotective agent such as hyaluronic acid, bone morphogenetic protein such as BMP-2, gene therapy agent, growth hormone, differentiation or modulation factor, immunosuppressant, immunostimulatory substance, DNA, RNA, nucleic acid, active proapoptotic agent, active adhesion promoter, receptor antagonist, and combinations of at least two of the stated active ingredients.

In another embodiment the combination, more particularly the first component and/or the second component, preferably the first component, comprises hyaluronic acid, i.e. unfunctionalized hyaluronic acid.

The combination, more particularly the first component and/or the second component, preferably the first component, preferably comprises a hyaluronic acid fraction of 0.1 wt % to 5 wt %, more particularly 0.2 wt % to 3 wt %, preferably 0.5 wt % to 2 wt %, based on the total weight of the two components dissolved in water.

In another embodiment the combination, more particularly the first component and/or the second component, preferably the first component, is free from hyaluronic acid.

In another embodiment the first component is in the form of an aqueous liquid, more particularly in the form of an aqueous solution or aqueous suspension, preferably in the form of an aqueous suspension. With particular preference the first component is in the form of an aqueous cell suspension, i.e. in the form of an aqueous suspension comprising cells. For possible cells, reference is made to the description hitherto.

In another embodiment the combination is in the form of a medical device or medical engineering product, preferably in the form of an implant.

The combination may more particularly be present in the form of a cell-free implant.

In an alternative embodiment the combination is in the form of a medicinal product for innovative therapies, more particularly in the form of a tissue engineering product (biotechnologically engineered tissue preparation) or implant that is inoculated or provided with cells.

In another embodiment the combination is a combination for use in the prophylaxis of pathological tissue adhesions, more particularly of tissue adhesions in the abdominal cavity or in other areas.

In another embodiment the combination is a combination for use in the treatment, more particularly reconstruction, of a cartilage defect, more particularly of an articular cartilage defect, preferably knee joint cartilage defect, or intervertebral disc defect, preferably lumbar intervertebral disc defect, more preferably lumbosacral intervertebral disc defect.

In another embodiment the combination is a combination for use in the treatment, more particularly reconstruction, of a defect of the annulus fibrosus and/or nucleus pulposus, preferably of the nucleus pulposus.

In another embodiment the combination is adapted for surgical administration, more particularly for minimally invasive administration. In other words, the combination, according to a further embodiment, is used for surgical, more particularly minimally invasive, administration.

In another embodiment the combination is adapted for facet joint infiltration, more particularly for periarticular and/or intraarticular facet joint infiltration, preferably intraarticular facet joint infiltration. In other words, the combination, according to a further embodiment, is used for facet joint infiltration, more particularly periarticular and/or intraarticular facet joint infiltration, preferably intraarticular facet joint infiltration.

In another embodiment the combination is in the form of a kit, more particularly in the form of a medical, preferably surgical, kit.

The invention according to a second aspect relates to a reaction product.

The reaction product is obtainable or producible by mixing a first component, comprising crosslinkable albumin, and a second component, comprising a polymer, where non-terminal monomer units of the polymer at least partially, more particularly only partially, comprise an albumin-crosslinking group, particularly by mixing a first component and a second component of a combination according to the first aspect of the invention.

The formation of the reaction product is based on a crosslinking reaction which proceeds between the crosslinkable albumin and the polymer, resulting in crosslinking of albumin molecules with one another via macromolecules of the polymer, preferably with formation of a hydrogel.

In accordance with the invention, therefore, it is particularly preferred if the reaction product is a hydrogel.

For further features and advantages of the reaction product, reference is made entirely, in order to avoid repetition, to the observations made in the context of the first aspect of the invention. The observations made there, especially in relation to the crosslinkable albumin and to the polymer, are equally valid (mutatis mutandis) for the reaction product.

According to a third aspect, the invention relates to a medical device.

The medical device comprises, spatially separate from one another, a first component, comprising crosslinkable albumin, and a second component, comprising a polymer, where non-terminal monomer units of the polymer at least partially, more particularly only partially, comprise an albumin-crosslinking group, more particularly a combination according to the first aspect of the invention.

The medical device is preferably an implant, more particularly a cell-free implant.

For further features and advantages of the medical device, reference is again made entirely, in order to avoid repetition, to the observations made in the context of the first aspect of the invention. The observations made there, especially in relation to the crosslinkable albumin and to the polymer, are equally valid (mutatis mutandis) for the medical device.

According to a fourth aspect, the invention relates to a medicinal product for innovative therapies.

The medicinal product for innovative therapies comprises, spatially separate from one another, a first component, comprising crosslinkable albumin, and a second component, comprising a polymer, where non-terminal monomer units of the polymer at least partially, more particularly only partially, comprise an albumin-crosslinking group, more particularly a combination according to the first aspect of the invention.

The medicinal product for innovative therapies is preferably a tissue engineering product (biotechnologically engineered tissue preparation) or an implant inoculated or provided with cells.

For further features and advantages of the medicinal product for innovative therapies, reference is again made entirely, in order to avoid repetition, to the observations made in the context of the first aspect of the invention. The observations made there, especially in relation to the crosslinkable albumin and to the polymer, are equally valid (mutatis mutandis) for the medicinal product for innovative therapies.

According to a fifth aspect, the invention relates to a kit.

The kit comprises, spatially separate from one another, a first component, comprising crosslinkable albumin, and a second component, comprising a polymer, where non-terminal monomer units of the polymer at least partially, more particularly only partially, comprise an albumin-crosslinking group, more particularly a combination according to the first aspect of the invention.

For further features and advantages of the kit, reference is again made entirely, in order to avoid repetition, to the observations made in the context of the first aspect of the invention. The observations made there, especially in relation to the crosslinkable albumin and to the polymer, are equally valid (mutatis mutandis) for the kit.

According to a sixth aspect, the invention relates to a discharge apparatus.

The discharge apparatus comprises, spatially separate from one another, a first component, comprising crosslinkable albumin, and a second component, comprising a polymer, where non-terminal monomer units of the polymer at least partially, more particularly only partially, comprise an albumin-crosslinking group, more particularly a combination according to the first aspect of the invention.

The discharge apparatus is preferably a multi-chamber discharge apparatus, more particularly a two-chamber discharge apparatus. The discharge apparatus may more particularly take the form of a double-barrel syringe.

For further features and advantages of the discharge apparatus, reference is again made entirely, in order to avoid repetition, to the observations made in the context of the first aspect of the invention. The observations made there, especially in relation to the crosslinkable albumin and to the polymer, are equally valid (mutatis mutandis) for the discharge apparatus.

According to a seventh aspect, the invention relates to a method for producing a combination, more particularly a combination according to the first aspect of the invention.

The method comprises the following steps:
providing a first component which comprises crosslinkable albumin, and, spatially separate therefrom,
providing a second component which comprises a polymer,
where non-terminal monomer units of the polymer at least partially, more particularly only partially, comprise an albumin-crosslinking group.

For further features and advantages of the method, reference is again made entirely, in order to avoid repetition, to the observations made in the context of the first aspect of the invention. The observations made there, especially in relation to the crosslinkable albumin and to the polymer, are equally valid (mutatis mutandis) for the method.

According to an eighth aspect, the invention relates to a method for producing a reaction product, preferably hydrogel, more particularly according to the second aspect of the invention.

The method comprises the following steps:
a) providing a first component which comprises crosslinkable albumin,
b) optionally adding cells, more particularly autologous cells, and/or active ingredients,
c) adding a crosslinking polymer,
where non-terminal monomer units of the polymer at least partially, more particularly only partially, comprise an albumin-crosslinking group.

For further features and advantages of the method, reference is again made entirely, in order to avoid repetition, to the observations made in the context of the first aspect of the invention. The observations made there, especially in relation to the crosslinkable albumin and to the polymer, are equally valid (mutatis mutandis) for the method.

According to a ninth aspect, the invention relates to the use of a polymer for crosslinking crosslinkable albumin, where non-terminal monomer units of the polymer at least partially, more particularly only partially, comprise an albumin-crosslinking group.

For further features and advantages of the polymer, reference is again made entirely, to the observations made in the context of the first aspect of the invention. The observations made there, especially in relation to the polymer and to the crosslinkable albumin, are equally valid (mutatis mutandis) for the use of the polymer.

According to a tenth aspect, the invention relates to a functionalized hyaluronic acid.

A particular feature of the functionalized hyaluronic acid is that every third repeating disaccharide unit to thousandth repeating disaccharide unit, more particularly every tenth repeating disaccharide unit to five-hundredth repeating disaccharide unit, preferably every twentieth repeating disaccharide unit to hundredth repeating disaccharide unit, of the functionalized hyaluronic acid is functionalized by an albumin-crosslinking group.

With particular preference glucuronic acid units of the hyaluronic acid and/or of the disaccharide units are functionalized by an albumin-crosslinking group.

In another embodiment the albumin-reactive groups are each linked via a linker unit covalently to the carboxy carbon atom of the glucuronic acid units.

The linker unit preferably possesses the formula I below

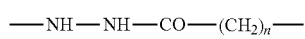 (formula I)

where n is an integer from 1 to 12, more particularly 2 to 4, preferably 2.

Alternatively, the linker unit preferably possesses the formula II below

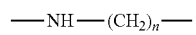 (formula II)

where n is an integer from 1 to 12, more particularly 2 to 4, preferably 2.

In one preferred embodiment the albumin-crosslinking group and/or the albumin-crosslinking groups is/are a nucleophilic group and/or nucleophilic groups, more particularly Michael donor group and/or Michael donor groups, preferably thiol group and/or thiol groups (SH group and/or SH groups) and/or thiolate group and/or thiolate groups (S$^-$ group and/or S$^-$ groups). The albumin-crosslinking group and/or the albumin-crosslinking groups is/are preferably a thiol group and/or thiol groups.

For further features and advantages of the functionalized hyaluronic acid, reference is made entirely to the observations made in the context of the first aspect of the invention. The observations made there are also valid (mutatis mutandis) for the hyaluronic acid.

Further features and advantages of the invention will be apparent from the following description of preferred embodiments in the form of examples, in conjunction with the dependent claims. Here, individual features may each be actualized alone or in combination with a plurality of other features. The embodiments described below serve merely to provide further illustration of the present invention, without restricting the invention to these embodiments.

EXAMPLES SECTION

1. Preparation of a Thiol-Functionalized Hyaluronic Acid

A thiol-functionalized hyaluronic acid with low loading was synthesized.

For this purpose, hyaluronic acid (average molecular weight 57 kDa) was activated with 1-ethyl-3-(3-dimethylaminopropyl)carbodiimide (EDC) at a pH of 4.75 and then modified with an excess of 3,3'-dithiobis(propanoic dihydrazide). Following removal of excess 3,3'-dithiobis(propanoic dihydrazide) by means of dialysis, the disulphide of the hydrazide coupled to the hyaluronic acid was reduced with tris(2-carboxyethyl)phosphine. Then low molecular mass components were removed by dialysis and the resulting functionalized hyaluronic acid was concentrated by ultrafiltration. In the hyaluronic acid ultimately obtained, approximately every 35th repeating disaccharide unit had a thiol group.

2. Preparation of Maleimide-Functionalized Serum Albumin of Bovine Origin 250 mg of human, leporine, bovine or ovine serum albumin (Sigma-Aldrich) were dissolved in 5 ml of 1 M sodium borate (pH 8.2).

Additionally, 106 mg of 3-maleimidopropionic acid N-hydroxysuccinimide ester (SMP, Obiter Research, Urbana, Ill., USA) were dissolved in 950 μl of dimethylformamide (DMF). Insoluble material was separated off by centrifugation. Then 500 μl of the supernatant were added to the albumin solution. This was followed by incubation at room temperature for a further 60 minutes. After that, 500 μl of 3 M sodium acetate (pH 4.7) were added and dialysis was carried out three times against 1 l of PBS on ice. The dialysate was subsequently concentrated by ultrafiltration (YM-3 membrane, Millipore) to a volume of 3.5 ml and subjected to sterilizing filtration.

3. Preparation of a Hydrogel

The thiol-functionalized hyaluronic acid prepared according to example 1 was added to the maleimide-functionalized albumin prepared according to example 2. Within a few minutes a hydrogel was obtained, which exhibited no separation tendency whatsoever.

4. Preparation of Thiol-Functionalized Carboxymethylcellulose

Thiol-functionalized carboxymethylcelluloses with low loading were synthesized.

For this purpose, carboxymethylcellulose (average molecular weight 90 kDa, degree of functionalization 0.75, i.e. 0.75 carboxyl groups per anhydroglucose unit) was dissolved in water and in various batches was activated respectively with 0.30 or 0.15 or 0.075 molar equivalent (based on carboxyl groups) of 4-(4,6-dimethoxy-1,3,5-triazin-2-yl)-4-methylmorpholinium chloride (DMTMM, CAS 3945-69-5) and then reacted with an excess of cystamine dihydrochloride at a pH of 6.5-7. Following removal of excess cystamine dihydrochloride by means of dialysis, the disulphide of the cystamine coupled to carboxymethylcellulose was reduced to the thiol using TCEP (tris(2-carboxyethyl)phosphine). Then low molecular mass components were removed by dialysis and the purified thiol-functionalized carboxymethylcellulose was concentrated by ultrafiltration. The thiol-functionalized carboxymethylcelluloses ultimately obtained had degrees of substitution of 3.6 and 2.8 and 2.1 thiol groups, respectively, per 100 anhydroglucose units.

5. Preparation of Hydrogels from Thiol-Functionalized Carboxymethylcelluloses

The thiol-functionalized carboxymethylcellulose prepared according to example 4 with a degree of substitution of 3.6 was added to a maleimide-functionalized albumin, prepared according to example 2, and PBS. The reactive groups (thiol and maleimide groups, respectively) were each calculated to a concentration of 2 mmol/L in the mixture. Within a few minutes, a hydrogel was obtained which exhibited no separation tendency whatsoever.

It was similarly possible in the same way, using the thiol-functionalized carboxymethylcellulose prepared according to example 4 with a degree of substitution of 2.1, to produce a hydrogel which exhibited no separation tendency whatsoever.

The invention claimed is:

1. A combination product comprising a first component and a second component, spatially separated from one another, wherein the first component comprises crosslinkable albumin and the second component comprises a polymer, wherein non-terminal monomer units of the polymer comprise at least partially an albumin-crosslinking group, wherein the polymer has a degree of substitution of 33 to 0.1 thiol groups per 100 monomer units, wherein the polymer is selected from the group consisting of hyaluronic acid functionalized by albumin-crosslinking groups and carboxymethylcellulose functionalized by albumin-crosslinking groups, wherein the albumin-crosslinking groups are thiol groups and the first component and the second component of the combination product are mixed to form a hydrogel.

2. The combination product of claim 1, wherein less than 20% of the non-terminal monomer units comprise an albumin-crosslinking group.

3. The combination product of claim 1, wherein every third to thousandth non-terminal monomer unit comprises an albumin-crosslinking group.

4. The combination product of claim 1, wherein the polymer is a polymer functionalized by the albumin-crosslinking groups.

5. The combination product of claim 1, wherein the polymer is a hyaluronic acid functionalized by albumin-crosslinking groups.

6. The combination product of claim 5, wherein glucuronic acid units of the hyaluronic acid are functionalized by albumin-crosslinking groups.

7. The combination product of claim 6, wherein the albumin-crosslinking groups are each linked covalently via a linker unit to a carboxy carbon atom of the glucuronic acid units.

8. The combination product of claim 7, wherein the linker unit possesses formula I or formula II below:

—NH—NH—CO—(CH$_2$)$_n$—  (formula I)

—NH—(CH$_2$)$_n$—  (formula II)

where n is an integer from 1 to 12.

9. The combination product of claim 1, wherein the albumin-crosslinking group and/or the albumin-crosslinking groups is or are a nucleophilic group and/or nucleophilic groups.

10. The combination product of claim 1, wherein the crosslinkable albumin is a functionalized albumin.

11. The combination product of claim 1, wherein the crosslinkable albumin is functionalized by at least one group selected from the group consisting of maleimide groups, vinyl sulfone groups, acrylate groups, alkyl halide groups, azirine groups, pyridyl groups, thionitrobenzoic acid groups, arylating groups, and combinations of at least two thereof.

12. The combination product of claim 1, wherein the crosslinkable albumin is maleimide-functionalized albumin.

13. The combination product of claim 1, wherein the first component further comprises cells, more particularly mammalian cells, preferably selected from the group consisting of musculoskeletal cells, metabolism-regulating glandular cells, islet cells, melatonin-producing cells, progenitor cells, stem cells, and combinations of at least two thereof.

14. The combination product of claim 1, wherein the first component is free from hyaluronic acid.

15. The combination product of claim 1, wherein the combination product is a medical device.

16. A kit comprising a combination product comprising a first component and a second component, spatially separated from one another, wherein the first component comprises crosslinkable albumin and the second component comprises a polymer, wherein non-terminal monomer units of the polymer comprise at least partially an albumin-crosslinking group, wherein the polymer has a degree of substitution of 33 to 0.1 thiol groups per 100 monomer units, wherein the polymer is selected from the group consisting of hyaluronic acid functionalized by albumin-crosslinking groups and carboxymethylcellulose functionalized by albumin-crosslinking groups, wherein the albumin-crosslinking groups are thiol groups and the first component and the second component of the combination product are mixed to form a hydrogel.

* * * * *